United States Patent [19]
Kohnert et al.

[11] Patent Number: 5,409,699
[45] Date of Patent: * Apr. 25, 1995

[54] COMPOSITIONS CONTAINING GLYCOSYLATED MOLECULES HAVING HUMAN TISSUE TYPE PLASMINOGEN ACTIVATOR ENZYMATIC ACTIVITY

[75] Inventors: Ulrich Kohnert, Habach; Rainer Rudolph, Weilheim, both of Germany

[73] Assignee: Boehringer Mannheim GmbH, Mannheim-Waldhof, Germany

[*] Notice: The portion of the term of this patent subsequent to Apr. 6, 2010 has been disclaimed.

[21] Appl. No.: 741,401

[22] PCT Filed: Dec. 19, 1990

[86] PCT No.: PCT/EP90/02252
  § 371 Date: Jul. 19, 1991
  § 102(e) Date: Jul. 19, 1991

[87] PCT Pub. No.: WO91/08767
  PCT Pub. Date: Jun. 27, 1991

[30] Foreign Application Priority Data
  Dec. 20, 1989 [DE] Germany ............... 39 42 142.2

[51] Int. Cl.⁶ ............... A61K 37/547; A61K 37/48; A61K 37/62; C12N 9/96
[52] U.S. Cl. ............... 424/94.64; 424/94.1; 424/94.3; 435/188
[58] Field of Search ............... 424/94.3, 94.65, 94.1, 424/94.64; 435/188

[56] References Cited

U.S. PATENT DOCUMENTS

| | | | |
|---|---|---|---|
| 4,927,630 | 5/1990 | Feder et al. | 424/94.63 |
| 4,929,444 | 5/1990 | Johnston et al. | 424/94.63 |
| 4,935,237 | 6/1990 | Higgins et al. | 429/94.63 |
| 4,960,702 | 10/1990 | Rig et al. | 435/226 |
| 4,980,165 | 12/1990 | Isaacs et al. | 424/94.63 |
| 4,985,245 | 1/1991 | Kikimoto et al. | 424/94.3 |
| 5,068,106 | 11/1991 | Pâques et al. | 424/94.3 |
| 5,100,666 | 3/1992 | Bell et al. | 424/94.63 |
| 5,112,609 | 5/1992 | Johnston et al. | 424/94.64 |
| 5,130,143 | 7/1992 | Strickland et al. | 424/94.63 |
| 5,132,214 | 7/1992 | Fedor et al. | 424/94.63 |
| 5,147,643 | 10/1992 | Heyneker | 424/94.63 |
| 5,149,533 | 10/1992 | Mulvihill et al. | 424/94.63 |

FOREIGN PATENT DOCUMENTS

| | | |
|---|---|---|
| 0156169 | 10/1985 | European Pat. Off. |
| 0211592 | 2/1987 | European Pat. Off. |
| 0217379A3 | 4/1987 | European Pat. Off. |
| 0228862 | 7/1987 | European Pat. Off. |
| 0297294 | 1/1989 | European Pat. Off. |
| 9061333 | 2/1990 | WIPO |

Primary Examiner—Douglas W. Robinson
Assistant Examiner—Kristin Larson
Attorney, Agent, or Firm—Felfe & Lynch

[57] ABSTRACT

The invention is a pharmaceutical composition containing a glycosylated protein having human tissue type plasminogen activator activity of at least 1.4 MU/ml, citrate, and at least one of a number of various compounds. The composition has a pH ranging from 4.5 to 9.

25 Claims, No Drawings

COMPOSITIONS CONTAINING GLYCOSYLATED MOLECULES HAVING HUMAN TISSUE TYPE PLASMINOGEN ACTIVATOR ENZYMATIC ACTIVITY

Human tissue type plasminogen activator (t-PA) possesses great therapeutic importance in the dissolving of blood coagula, e.g. in the case of heart infarcts. t-PA brings about the dissolution of blood coagula by the activation of plasminogen to plasmin. Plasmin in turn dissolves fibrin, the main component of the protein matrix of coagulated blood.

Natural t-PA is composed of several functional domains F, E, K1, K2 and P. The domain P contains the proteolytically active region which brings about the cleavage of plasminogen to plasmin. Recombinant preparations of t-PA or of various t-PA muteins, in which one or more of the domains F, E, K1 and K2 are deleted, in eukaryotic and prokaryotic cells are already known. In contradistinction to natural t-PA, t-PA derivatives are synthesised from prokaryotes in non-glycosylated form.

Glycosylated proteins with t-PA activity only dissolve in low concentrations in the buffers usually employed for the solubilisation of proteins, such as e.g. 50 mmole/l. Na citrate, 50 mmole/l. phosphate or physiological NaCl solution. However, for their use as therapeutically-active material, protein solutions with a higher t-PA activity of at least 1.4 MU/ml., preferably of 1.4 MU/ml. to 10 MU/ml should be used.

It is known from EP-A 0 217 379 that neutral or slightly alkaline arginine formulations can increase the solubility of t-PA. A disadvantage of this process is, however, the low stability of highly concentrated solutions under neutral or slightly alkaline conditions.

U.S. Pat. No. 4,777,043 discloses a pharmaceutical composition with human t-PA and a pharmaceutically compatible argininium ion-containing buffer with a chloride ion concentration of up to 0.3 mole/l. EP-A 0 156 169, EP-A 0 303 351 and EP-A 0 297 294 disclose further possibilities of solubilising proteins with t-PA activity in buffers with particular amino acids, their salts, derivatives and homologues. Furthermore, t-PA can be stabilised by addition of gelatin according to EP-A 0 123 304, by addition of albumin according to EP-A 0 112 940 or by addition of a polysulphuric acid ester of a saccharide or of a sulphated sugar according to EP-A 0 198 321. PCT/US88/04402 discloses a process for increasing t-PA solubility, wherein one uses an aqueous medium with a basic amino acid, especially arginine, in a concentration of 0.02 to 0.2 mole/l., together with a citric acid group in a concentration of 0.02 to 0.08 mole/l. at a pH value of 5 to 8.

However, these various compositions are not generally suitable for all proteins with t-PA properties. Thus, it was ascertained that various glycosylated or non-glycosylated t-PA variants possess solubility properties which differ greatly from one another.

Consequently, it is the aim of the invention to develop pharmaceutical compositions which contain e.g., glycosylated t-PA or t-PA muteins with an activity of more than 1.4 MU/ml., whereby the t-PA is to be stable over a comparatively long period of time. The unit U is defined according to WHO, National Institute for Biological Standards and Control (cf. H. Lill, ZGIMAL, 42 (1987), 478–486).

According to the invention, the aim is solved by a pharmaceutical composition of a glycosylated protein with t-PA activity with an activity of at least 1.4 MU/ml. with a pH value of 4.5 to 9, whereby this composition contains citrate and at least one compound from the group consisting of
a) ascorbic acid,
b) EDTA,
c) amino compounds of the formula $$R^1R^2N-R-X$$

whereby X=SO$_3$H, H, NH$_2$ or OH, R=C$_1$-C$_9$-alkylene, C$_3$-C$_6$-cycloalkylene or benzylidene and R$^1$ and R$^2$, independently of one another, are H or C$_1$-C$_3$-alkyl,
d) guanidinobutyric acid,
e) dimethylbiguanide,
f) 7-aminoheptanoic acid, 8-aminooctanoic acid, p-aminomethylbenzoic acid, δ-aminovaleric acid, γ-aminobutyric acid,
g) glucosamine, fructose,
h) pyrimidine nucleosides and pyrimidine nucleotides,
i) carboxylic acids substituted with one or more hydroxyl, keto and/or further carboxyl group.

The concentration of the citrate ions in the pharmaceutical preparation according to the invention amounts to at least 5 mmole/l., preferably from 5 to 100 mmole/l. Especially preferred is a concentration of the citrate ions of 50 mmole/l. Depending upon the alkalinity of the compounds added, the pH value is adjusted with HCl or a base, such as e.g. NaOH or KOH.

It has proven to be suitable to adjust the pH value of the alkaline citrate solutions with HCl, i.e., so that the composition additionally contains chloride ions. In the presence of chloride ions, highly concentrated solutions of t-PA or of t-PA derivatives are surprisingly substantially more stable than they are, e.g. in the presence of phosphate ions. The pH value of acidic citrate solutions is usually adjusted with NaOH.

Suitable for a composition according to the invention is a pH value between 4.5 and 9. A pH value of 6 is preferred.

According to the present invention, glycosylated protein with t-PA activity is understood to be a non-modified t-PA from eukaryotic organisms, as well as all glycosylated t-PA muteins. Examples of t-PA muteins are described e.g. by Harris (Protein Engineering, 1 (1987), 449–458).

The composition according to the invention preferably contains native glycosylated t-PA with the domains F, E, K1, K2 and P from CHO cells (prepared according to WO 87/02673). However, all other t-PA variants from eukaryotes are also suitable.

For a composition according to the invention, amino acids taurine, 4-aminobutanol-1, 5-aminopentanol-1, 6-aminohexanol-1, 1,9-diaminononane, 1,8-diaminooctane, 1,7-diaminoheptane, 1,6-diaminohexane, 1,5-diaminopentane, 1,4-aminobutane or 1,3-aminopropane are preferred. The preferred concentration for taurine and analogous compounds amounts to 0.1 to 0.5 mole/l., with concentrations of 0.1 to 0.3 mole/l being preferred. The other above-mentioned compounds (α,ω-diamines and α-ω-aminoalcohols) are preferably used at concentrations of 10 to 100 mmole/l.

For a carboxylic acid which is substituted with one or more hydroxyl, keto and/or further carboxyl groups, one uses e.g. malic acid, lactic acid, fumaric acid or 2-oxoglutaric acid. These substances are preferably used at concentrations of from 1 mmole/l. to 1000 mmole/l. Especially preferred is a concentration of from 10 to 500 mmole/l.

Guanidinobutyric acid is preferably used at a concentration of from 10 to 200 mmole/l. Especially preferred is a concentration of from 50 to 100 mmole/l. For dimethylbiguanide, the concentration amounts to 50 to 400 mmole/l., preferably 100 to 300 mmole/l.

One uses 7-aminoheptanoic acid, 8-aminooctanoic acid, δ-aminovaleric acid, γ-aminobutyric acid or p-aminomethylbenzoic acid at a concentration of from 0.5 to 20 mmole/l. Especially preferred is a concentration of from 1 to 10 mmole/l. Surprisingly, in even small molar excess (10 to 40 fold), these substances lead to outstanding solubility of glycosylated t-PA derivatives.

Glucosamine and fructose are preferably used in concentrations of 1 to 500 mmole/l. Especially preferred concentrations range from 10 to 300 mmole/l.

Pyrimidne nucleoside or pyrimidine nucleotide are suitable e.g. thymidine, cytosine and uridine or the corresponding nucleotides. These substances are preferably used in concentrations of 1 to 300 mmole/l. Especially preferred concentrations range from 10 to 300 mmole/l.

Furthermore, a subject of the invention is a composition according to the invention which additionally contains one or more amino acids, especially histidine.

In the following is set out a series of especially preferred preparations according to the present invention.

One formulation contains 50 mmole/l. Na citrate, pH 6 and 0.1 to 0.3 mole/l. taurine. Also preferred is a formulation with 50 mmole/l. Na citrate, pH 6 and 0.2 to 0.3 mole/l. ascorbic acid.

Also preferred is a formulation with 50 mmole/l. Na citrate/HCl, pH 6 and 1 mmole/l. to 10 mmole/l. 7-aminoheptanoic acid, 8-aminooctanoic acid, δ-aminovaleric acid, γ-aminobutyric acid or p-aminomethylbenzoic acid.

Furthermore, especially preferred formulations contain 50 mmole/l. Na citrate/HCl, pH 6.0 and 50 to 100 mmole/l. guanidinobutyric acid.

Also preferred is a formulation which contains 50 mmole/l. Na citrate, pH 6 and 10 to 100 mmole/l. EDTA. Furthermore, a further formulation contains 50 mmole/l. Na citrate/HCl, pH 6, and 100 to 300 mmole/l. dimethylbiguanide.

A further formulation contains 50 mmole/l. Na citrate, pH 6 and 10 to 300 mmole/l. thymidine, cytosine or uridine.

Furthermore, a further formulation contains 50 mmole/l. Na citrate/HCl, pH 6 and 10 to 100 mmole/l. 4-aminobutanol-1, 5-aminopentanol-1, 6-aminohexanol-1, 1,9-diaminononane, 1,8-diaminooctane, 1,7-diaminoheptane, 1,6-diatninohexane, 1,5-diaminopentane, 1,4-diaminobutane or 1,3-aminopropane.

A further formulation contains 50 mmole/l. Na citrate/HCl, pH 6 and 10 to 300 mmole/l. fructose or glucosamine.

Finally, a further formulation contains 50 mmole/l. Na citrate, pH 6 and 10 to 500 mmole/l. malic acid, lactic acid, fumaric acid or 2-oxoglutaric acid.

Combinations of several of the above-mentioned compounds with citrate also bring about good solubility of glycosylated proteins with t-PA activity, especially of t-PA from CHO cells.

The subject of the invention is also a medicament based on a glycosylated protein with t-PA activity as active material in solution or as lyophilisate with the given active materials and possibly also further pharmaceutically compatible additive, adjuvant, carrier and filling materials.

The pharmaceutical preparations according to the invention are preferably used as injection and infusion solutions. These can be made, e.g., from a solution ready for injection which is made available and which possesses the composition according to the invention. However, it is also possible to make available the pharmaceutical preparations in the form of lyophilisates. These are then reconstituted with per se known agents or solutions suitable for injection purposes. As injection medium, water is preferably used which contains the additives usual in the case of injection solutions, such as stabilising agents, solubilising agents, buffers and isotonic additives, for example a physiological NaCl concentration. Such additives are, for example, mannitol, tartrate or citrate buffer, ethanol, complex formers, such as e.g. ethylenediamine-tetraacetic acid and its non-toxic salts, as well as high molecular polymers, such as liquid polyethylene oxide, for viscosity regulation. Liquid carrier materials for injection solutions must be sterile and are preferably filled into ampules.

Finally, the present invention also comprises the use of glycosylated proteins with t-PA activity for the production of pharmaceutical preparations according to the invention.

The following Example is to explain further the concrete carrying out of the invention.

Example

Solubility of CHO-tPA

Purified CHO-tPA (dissolved in 0.5 mole/l. arginine/$H_3PO_4$, pH 7.3) is concentrated by ultra-filtration over a YM 10 membrane (Amicon). In each case, 1 ml. of the concentrate (activity: 6.6 MU/ml.) is dialysed against the buffers set out in Table 1. After centrifuging of the samples, the enzymatic activity is measured in the clear supernatant.

The enzymatic activity is given as volume unit in MU/ml. and as total activity in MU.

The measurement of the tPA activity can thereby be determined in the usual way by cleavage of a chromogenic substrate (H. Lill, ZGIMAL, 42 (1987), 78–486).

The unit U is one unit of the activity according to definition of the WHO, National Institute for Biological Standards and Control.

TABLE 1

| buffer | activity MU/ml | MU |
|---|---|---|
| 50 mmole/l. Na citrate/NaOH, pH 6 0.3 mol/l. taurine | 4.60 | 5.52 |
| 50 mmole/l. Na citrate/HCl, pH 6 0.3 mol/l. fructose | 1.65 | 1.73 |
| 50 mmole/l. Na citrate/NaOH, pH 6 0.3 mole/l. ascorbic acid | 4.76 | 4.76 |
| 50 mole/l. Na citrate/HCl, pH 6 10 mmole/l. p-aminomethylbenzoic acid | 5.58 | 6.40 |
| 50 mmole/l. Na citrate/HCl, pH 6 300 mmole/l. dimethylbiguanide | 5.91 | 6.50 |
| 0.05 mole/l. Tris/HCl, pH 7.2 | 0.02 | 0.04 |
| 50 mmole/l. $NH_4HCO_3$ | 0.06 | 0.09 |
| 50 mmole/l. $Na_2HPO_4/H_3PO_4$, pH 6 | 0.14 | 0.19 |
| 50 mmole/l. Na citrate/HCl, pH 6 10 mmole/l. 7-aminoheptanoic acid | 5.07 | 7.00 |
| 50 mmole/l. Na citrate/HCl, pH 6 10 mmole/l. δ-aminovaleric acid | 4.00 | 4.80 |
| 50 mmole/l. Na citrate/HCl, pH 6 10 mmole/l. γ-aminobutyric acid | 3.18 | 4.13 |
| 50 mmole/l. Na citrate/HCl, pH 6 50 mmole/l. 1,6-diaminohexane | 5.20 | 6.30 |

TABLE 1-continued

| buffer | activity MU/ml | MU |
|---|---|---|
| 50 mmole/l. Na citrate/HCl, pH 6<br>50 mmole/l. 5-aminopentanol | 6.00 | 6.00 |
| 50 mmole/l. Na citrate/HCl, pH 6<br>50 mmole/l. guanidinobutyric acid | 3.24 | 3.90 |
| 50 mmole/l. Na citrate/NaOH, pH 6<br>50 mmole/l. EDTA | 3.42 | 3.76 |
| 50 mmole/l. Na citrate/NaOH, pH 6<br>100 mmole/l. EDTA | 5.07 | 5.8 |
| 50 mmole/l. Na citrate/HCl, pH 6<br>0.3 mole/l. glucosamine | 3.42 | 3.76 |
| 50 mmole/l. Na citrate/HCl, pH 6<br>0.1 mole/l. thymidine | 2.40 | 2.88 |
| 50 mmole/l. Na citrate/HCl, pH 6 | 0.79 | 0.98 |
| 50 mmole/l. Na citrate/NaOH, pH 6<br>0.3 mole/l. fumaric acid | 2.97 | 2.97 |

We claim:

1. A pharmaceutical composition consisting essentially of:
   (i) glycosylated tissue plasminogen activator having F, E, K1, K2, and P domains, said t-PA having an activity of at least 1.4 MU/ml,
   (ii) citrate, and
   (iii) at least one compound selected from the group consisting of:
   (a) ascorbic acid;
   (b) EDTA;
   (c) an amino compound of the formula

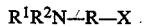

wherein X is $SO_3H$, H, $NH_2$, or OH, R is a $C_1$-$C_9$-alkylene, $C_3$-$C_6$-cycloalkylene or benzylidene, $R^1$ is H or $C_1$-$C_3$ alkyl and $R^2$ is H or $C_1$-$C_3$ alkyl;
   (d) guanidinobutyric acid;
   (e) dimethylbiguanide;
   (f) 7-aminoheptanoic acid;
   (g) 8-aminooctanoic acid;
   (h) p-aminomethylbenzoic acid;
   (i) δ-aminovaleric acid;
   (j) γ- aminobutyric acid;
   (k) glucosamine;
   (l) fructose;
   (m) a pyrimidine nucleoside;
   (n) a pyrimidine nucleotide; and
   (o) a carboxylic acid selected from the group consisting of malic acid, lactic acid, fumaric acid and 2-oxoglutaric acid, wherein said composition is at a pH of from 4.5 to 9.

2. The pharmaceutical composition of claim 1, wherein said amino compound is selected from the group consisting of taurine, 4-aminobutanol-1, 5-aminopentanol-1, 6-aminohexanol-1, 1,9-diaminononane, 1,8-diaminooctane, 1,7-diaminoheptane, 1,6-diaminohexane, 1,5-diaminopentane, 1,4-diaminobutane and 1,3-diaminopropane.

3. The pharmaceutical composition of claim 1, wherein said citrate is present at a concentration of from 5 to 100 mmole/l.

4. The pharmaceutical composition of claim 3, wherein said citrate is present at a concentration of 50 mmole/l.

5. The pharmaceutical composition of claim 1, further consisting essentially of chloride ions.

6. The pharmaceutical composition of claim 1, wherein said composition has a pH of 6, said citrate is present at a concentration of 50 mmol/l Na citrate, and said ascorbic acid is present at a concentration of from 0.1 to 1.0 mole/l.

7. The pharmaceutical composition of claim 6, wherein said ascorbic acid is present at a concentration of from 0.2 to 0.3 mole/l.

8. The pharmaceutical composition of claim 1, wherein said composition has a pH of 6, said citrate is present at a concentration of 50 mmol/l Na citrate and said EDTA is present at a concentration of from 1 to 200 mmol/l.

9. The pharmaceutical composition of claim 8, wherein said EDTA is present at a concentration of from 10 to 100 mmol/l.

10. The pharmaceutical composition of claim 2, wherein said composition has a pH of 6, said citrate is present in a concentration of 50 mmol/l Na citrate and said taurine is present at a concentration of from 0.1 to 0.5 mol/l.

11. The pharmaceutical composition of claim 10, wherein said taurine is present in a concentration of from 0.1 to 0.3 mol/l.

12. The pharmaceutical composition of claim 2, wherein said composition has a pH of 6, said citrate is present at a concentration of 50 mmol/l Na citrate/HCl, and said compound selected from the group consisting of:
   (a) 4-aminobutanol-1,
   (b) 5-aminopentanol-1,
   (c) 6-aminohexanol-1,
   (d) 1,3-diaminopropane,
   (e) 1,4-diaminobutane,
   (f) 1,5-diaminopentane,
   (g) 1,6-diaminohexane,
   (h) 1,7-diaminoheptane,
   (i) 1,8-diaminooctane, and
   (j) 1,9-diaminononane,
   is present at a concentration of 10 to 100 mmol/l.

13. The pharmaceutical composition of claim 1, wherein said composition has a pH of 6, said citrate is present at a concentration of 50 mmol/l Na citrate/HCl and said guanidinobutyric acid is present at a concentration of from 10–200 mmol/l.

14. The pharmaceutical composition of claim 13, wherein said guanidinobutyric acid is present at a concentration of from 50 to 100 mol/l.

15. The pharmaceutical composition of claim 1, wherein said composition has a pH of 6, said citrate is present at a concentration of 50 mmol/l Na citrate/HCl and said dimethylbiguanide is present at a concentration of from 50 to 400 mmol/l.

16. The pharmaceutical composition of claim 15, wherein said dimethylbiguanide is present at a concentration of from 100 to 300 mmol/l.

17. The pharmaceutical composition of claim 1, wherein said composition has a pH of 6, said citrate is present at a concentration of 50 mmol/l Na citrate and an acid selected from the group consisting of:
   (a) 7-aminoheptanoic acid,
   (b) 8-aminooctanoic acid,
   (c) δ-aminovaleric acid,
   (d) γ-aminobutyric acid, and
   (e) p-aminomethylbenzoic acid,
   wherein said acid is present at a concentration of from 0.5 to 20 mmol/l.

18. The pharmaceutical composition of claim 17, wherein said acid is present at concentration of from 1 to 10 mmol/l.

19. The pharmaceutical composition of claim 1, wherein said composition has a pH of 6, said citrate is present at a concentration of 50 mmol/l Na citrate/HCl and said glucosamine or fructose is present at a concentration of from 1 to 500 mmol/l.

20. The pharmaceutical composition of claim 19, wherein said glucosamine or fructose is present at a concentration of from 10 to 300 mmol/l.

21. The pharmaceutical composition of claim 1, wherein said composition has a pH of 6 and a compound selected from the group consisting of thymidine, cytosine and uridine is present at a concentration of from 1 to 300 mmol/l.

22. The pharmaceutical composition of claim 21, wherein said thymidine, cytosine or uridine is present at a concentration of from 10 to 300 mmol/l.

23. The pharmaceutical composition of claim 1, wherein said composition has a pH of 6 said citrate is present at a concentration of 50 mmol/l Na citrate and a carboxylic acid selected from the group consisting of malic acid, lactic acid, fumaric acid and 2-oxoglutaric acid, wherein said acid is present at a concentration of from 1 to 1000 mmol/l.

24. The pharmaceutical composition of claim 23, wherein said carboxylic acid is present at a concentration of from 10 to 500 mmol/l.

25. The pharmaceutical composition of claim 1, further comprising a pharmaceutically acceptable additive, adjuvant, or carrier.

* * * * *